United States Patent
Esch

(10) Patent No.: US 7,485,144 B2
(45) Date of Patent: Feb. 3, 2009

(54) METHODS OF ADJUSTING THE POWER OF AN INTRAOCULAR LENS

(75) Inventor: Victor Esch, Albuquerque, NM (US)

(73) Assignee: PowerVision, Inc., Belmont, CA (US)

( * ) Notice: Subject to any disclaimer, the term of this patent is extended or adjusted under 35 U.S.C. 154(b) by 0 days.

(21) Appl. No.: 11/520,204

(22) Filed: Sep. 12, 2006

(65) Prior Publication Data

US 2007/0010880 A1    Jan. 11, 2007

Related U.S. Application Data

(62) Division of application No. 10/734,514, filed on Dec. 12, 2003, now Pat. No. 7,122,053.

(60) Provisional application No. 60/433,046, filed on Dec. 12, 2002.

(51) Int. Cl.
*A61F 2/16* (2006.01)
(52) U.S. Cl. .............. 623/6.13; 623/6.22; 623/6.37
(58) Field of Classification Search ............... 623/4.1, 623/6.13, 6.22, 6.34, 6.37, 6.4, 6.43
See application file for complete search history.

(56) References Cited

U.S. PATENT DOCUMENTS

| 4,253,199 A | 3/1981 | Banko |
| 4,304,895 A | 12/1981 | Loshaek |
| 4,373,218 A | 2/1983 | Schachar |
| 4,409,691 A | 10/1983 | Levy |
| 4,435,856 A | 3/1984 | L'Esperance |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,615,701 A | 10/1986 | Woods |
| 4,685,921 A | 8/1987 | Peyman |
| 4,685,922 A | 8/1987 | Peyman |
| 4,693,717 A | 9/1987 | Michelson |
| 4,731,078 A | 3/1988 | Stoy et al. |

(Continued)

FOREIGN PATENT DOCUMENTS

JP    9294754    11/1997

(Continued)

OTHER PUBLICATIONS

Esch et al; U.S. Appl. No. 11/844,108 entitled "Accommodating Intraocular Lens System and Method" filed Aug. 23, 2007.

(Continued)

*Primary Examiner*—William H. Matthews
(74) *Attorney, Agent, or Firm*—Shay Glenn LLP

(57) ABSTRACT

An accommodating intraocular lens is provided, in which optical parameters are altered in-situ using forces applied by the ciliary muscles, and in which a lens body carries an actuator separating two fluid-filled chambers having either the same index of diffraction or different indices of refraction. The actuator causes the relative volumes of fluid within an optic element of the lens to change, thereby altering the optical power of the lens.

20 Claims, 7 Drawing Sheets

U.S. PATENT DOCUMENTS

| | | |
|---|---|---|
| 4,731,080 A | 3/1988 | Galin |
| 4,787,903 A | 11/1988 | Grendahl |
| 4,790,847 A | 12/1988 | Woods |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turely |
| 4,902,293 A | 2/1990 | Feaster |
| 4,932,966 A | 6/1990 | Christie et al. |
| 4,946,469 A | 8/1990 | Sarafarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 5,015,254 A | 5/1991 | Greite |
| 5,035,710 A | 7/1991 | Nakada et al. |
| 5,047,051 A | 9/1991 | Cumming |
| 5,066,301 A | 11/1991 | Wiley |
| 5,145,935 A | 9/1992 | Hayashi |
| 5,152,789 A | 10/1992 | Willis |
| 5,171,266 A | 12/1992 | Wiley et al. |
| 5,201,763 A | 4/1993 | Brady et al. |
| 5,213,579 A | 5/1993 | Yamada et al. |
| 5,235,003 A | 8/1993 | Ward et al. |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,405,386 A | 4/1995 | Rheinish et al. |
| 5,443,506 A | 8/1995 | Garabet |
| 5,444,106 A | 8/1995 | Zhou et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,665,822 A | 9/1997 | Bitler et al. |
| 5,674,282 A | 10/1997 | Cumming |
| 5,697,973 A | 12/1997 | Peyman et al. |
| 5,702,441 A | 12/1997 | Zhou |
| 5,774,273 A | 6/1998 | Bornhorst |
| 5,843,188 A | 12/1998 | McDonald |
| 5,891,931 A | 4/1999 | Leboeuf et al. |
| 5,928,282 A | 7/1999 | Nigam |
| 5,984,962 A | 11/1999 | Anello et al. |
| 6,013,101 A | 1/2000 | Israel |
| 6,015,842 A | 1/2000 | Leboeuf et al. |
| 6,117,171 A | 9/2000 | Skottum |
| 6,124,980 A | 9/2000 | Cerbell |
| 6,139,576 A | 10/2000 | Doyle et al. |
| 6,176,878 B1 | 1/2001 | Gwon et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,217,612 B1 | 4/2001 | Woods |
| 6,225,367 B1 | 5/2001 | Chaouk et al. |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,388,043 B1 | 5/2002 | Langer et al. |
| 6,406,494 B1 | 6/2002 | Laguette et al. |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,503,276 B2 | 1/2003 | Lang et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,592,621 B1 | 7/2003 | Domino |
| 6,599,317 B1 | 7/2003 | Weinschenk, III et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,749,632 B2 | 6/2004 | Sandstedt et al. |
| 6,827,738 B2 | 12/2004 | Willis et al. |
| 6,836,374 B2 | 12/2004 | Esch et al. |
| 6,860,601 B2 | 3/2005 | Shadduck |
| 6,899,732 B2 | 5/2005 | Zadno-Azizi et al. |
| 6,926,736 B2 | 8/2005 | Peng et al. |
| 6,935,743 B2 | 8/2005 | Shadduck |
| 6,966,649 B2 | 11/2005 | Shadduck |
| 6,969,403 B2 | 11/2005 | Peng et al. |
| 7,068,439 B2 | 6/2006 | Esch |
| 7,122,053 B2 | 10/2006 | Esch |
| 7,217,288 B2 | 5/2007 | Esch et al. |
| 7,264,351 B2 | 9/2007 | Shadduck |
| 7,278,739 B2 | 10/2007 | Shadduck |
| 2001/0001836 A1 | 5/2001 | Cumming |
| 2001/0016771 A1 | 8/2001 | Cumming |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0161434 A1 | 10/2002 | Laguette et al. |
| 2002/0193876 A1 | 12/2002 | Lang et al. |
| 2003/0003295 A1 | 1/2003 | Dreher et al. |
| 2003/0018384 A1 | 1/2003 | Valyunin et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0187505 A1 | 10/2003 | Liao |
| 2003/0199977 A1 | 10/2003 | Cumming |
| 2004/0001180 A1 | 1/2004 | Epstein |
| 2004/0006386 A1 | 1/2004 | Kelman |
| 2004/0006387 A1 | 1/2004 | Kelman |
| 2004/0008419 A1 | 1/2004 | Schachar |

| | | |
|---|---|---|
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082994 A1 | 4/2004 | Woods et al. |
| 2004/0085511 A1 | 5/2004 | Uno et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0190153 A1 | 9/2004 | Esch |
| 2005/0021139 A1 | 1/2005 | Shadduck |
| 2005/0119740 A1 | 6/2005 | Esch et al. |
| 2005/0149183 A1 | 7/2005 | Shadduck |
| 2005/0264756 A1 | 12/2005 | Esch |
| 2006/0041307 A1 | 2/2006 | Esch et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0203578 A1 | 8/2007 | Scholl et al. |
| 2007/0213817 A1 | 9/2007 | Esch et al. |
| 2007/0299487 A1 | 12/2007 | Shadduck |
| 2008/0015689 A1 | 1/2008 | Esch et al. |

FOREIGN PATENT DOCUMENTS

| | | |
|---|---|---|
| JP | 11276509 | 10/1999 |
| WO | WO 97/06751 A | 2/1997 |
| WO | WO 00/41650 A1 | 7/2000 |
| WO | WO 01/97742 A2 | 12/2001 |
| WO | WO 2004/010895 | 2/2004 |
| WO | WO 2004/046768 A2 | 6/2004 |
| WO | WO 2004/072689 A2 | 8/2004 |

OTHER PUBLICATIONS

Smith et al; U.S. Appl. No. 11/844,087 entitled "Accommodating Intraocular Lens System Having Spherical Aberration Compensation and Method," filed Aug. 23, 2007.

Wyant et al; "Basic Wavefront Aberration Theory for Optical Metrology," Applied Optics and Optical Engineering, vol. XI, 1992:1-13.

Your, Jingjong; U.S. Appl. No. 12/034,942 entitled "Polymeric materials suitable for ophthalmic devices and methods of manufacture," filed Feb. 21, 2008.

Your, Jingjong; U.S. Appl. No. 12/177,720 entitled "Lens material and methods of curing with UV light," filed Jul. 22, 2008.

Smiley et al.; U.S. Appl. No. 12/177,857 entitled "Accommodating intraocular lenses and methods of use," filed Jul. 22, 2008.

Smiley et al.; U.S. Appl. No. 12/178,304 entitled "Post-implant accommodating lens modification," filed Jul. 23, 2008.

Smiley et al.; U.S. Appl. No. 12/17,.565 entitled "Lens delivery system," filed Jul. 23, 2008.

Choi et al.; U.S. Appl. No. 12/178,454 entitled "Systems and methods for testing intraocular lenses," filed Jul. 23, 2008.

Baughman et al., "Negative poisson's ratios for extreme states fo matter," Science, vol. 288, pp. 1028-2022, Jun. 16, 2000.

Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.

Jeon et al., "Shape memory and nonstructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2899, Mar. 26, 2001.

Lakes, "Lateral deformations in extreme matter," Science, vol. 288, pp. 1976, Jun. 2000.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

Mather et al., "Strain recovery in POSS hybrid thermoplastics," Polymer Preprints, vol. 41, No. 1, pp. 528-529, 2000.

Rosakis et al., "Microbuckling instability in elastomeric cellular sollids," J. Materials Science, vol. 28, pp. 4667-4672, 1993.

Takahashi et al., "Structure and properties of shape-memory polyurethane block copolymers," Journal of Applied Polymer Science, vol. 60, pp. 1061-1069, 1996.

Tobushi et al., "Thermomechanical properties of shape memory polymers of polyurethane series and their applications," Journal de Physique IV, Colloque C1, vol. 6, pp. 377-384, 1996.

Xu et al., "Basic negative poisson's ratio microstructures by soft lithography," Advanced Materials, vol. 11, No. 14, 1999, pp. 1186-1189, 1999.

METHODS OF ADJUSTING THE POWER OF AN INTRAOCULAR LENS

REFERENCE TO RELATED APPLICATIONS

The present application is a divisional application of U.S. application Ser. No. 10/734,514, filed on Dec. 12, 2003, now U.S. Pat. No. 7,122,053 which claims the benefit of U.S. provisional application No. 60/433,046, filed on Dec. 12, 2002, the disclosures of which are hereby incorporated by reference.

FIELD OF THE INVENTION

The present invention relates to intraocular lenses ("IOLs") having optical parameters that are changeable in-situ. More particularly, the invention has applications in IOLs for in-capsule implantation for cataract patients, wherein forces applied by the ciliary muscles in the eye induce movement of fluid media within the interior of the IOL, thereby altering an optical power of the lens to provide accommodation.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule supported by the ciliary muscles, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein), move between a relaxed state (corresponding to the moderately convex shape) to a contracted state (corresponding to the highly convex shape). Because the lens itself is composed of viscous, gelatinous transparent fibers, arranged in an "onion-like" layered structure, forces applied to the capsule by the ciliary muscles cause the lens to change shape.

Isolated from the eye, the relaxed capsule and lens take on a spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter muscular mode. Accordingly, when the ciliary muscles are relaxed, the capsule and lens are pulled about the circumference to a larger diameter, thereby flattening the lens, whereas when the ciliary muscles are contracted the lens and capsule relax somewhat and assume a smaller diameter that approaches a more spherical shape. This mechanism, called the "ciliary process" increases the diopter power of the lens.

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition know as "presbyopia". Because the imaging distance is fixed, presbyopia typically entails the need for bi-focals to facilitate near and far vision.

Apart from age-related loss of accommodation ability, such loss is innate to the placement of IOLs for the treatment of cataracts. IOLs are generally single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability.

Although previously known workers in the field of accommodating IOLs have made some progress, the relative complexity of the methods and apparatus developed to date have prevented widespread commercialization of such devices. Previously known these devices have proved to complex to be practical to construct or have achieved only limited success, due to the inability to provide accommodation of more than 1-2 diopters.

U.S. Pat. No. 5,443,506 to Garabet describes an accommodating fluid-filled lens wherein electrical potentials generated by contraction of the ciliary muscles cause changes in the index of refraction of fluid carried within a central optic portion. U.S. Pat. No. 4,816,031 to Pfoff discloses an IOL with a hard PMMA lens separated by a single chamber from a flexible thin lens layer that uses microfluid pumps to vary a volume of fluid between the PMMA lens portion and the thin layer portion and provide accommodation. U.S. Pat. No. 4,932,966 to Christie et al. discloses an intraocular lens comprising a thin flexible layer sealed along its periphery to a support layer, wherein forces applied to fluid reservoirs in the haptics vary a volume of fluid between the plurality of layers to provide accommodation.

Although fluid-actuated mechanisms such as described in the aforementioned patents have been investigated, accommodating lenses currently nearing commercialization, such as developed by Eyeonics, Inc. (formerly C&C Vision, Inc.) of Aliso Viejo, Calif., rely ciliary muscle contraction of the IOL haptics to move the optic towards or away from the retina to adjust the focus of the device.

In view of the foregoing, it would be desirable to provide apparatus and methods that restore appropriate optical focusing power action to the human eye.

It further would be desirable to provide methods and apparatus wherein a dynamic lens surface may be effectively manipulated by the ciliary muscular mechanisms within the eye.

It still further would be desirable to provide methods and apparatus that utilize pressure applied by the accommodating muscular action to obtain mechanical deviation of an optical surface of the IOL. In particular, it would be desirable to provide an IOL in which muscular pressure may be applied through one or more actuators to obtain a mechanical advantage.

SUMMARY OF THE INVENTION

In view of the foregoing, it is an object of the present invention to provide apparatus and methods that restore appropriate optical focusing power action to the human eye.

It is a further object of this invention to provide methods and apparatus wherein a dynamic lens surface may be effectively manipulated by the ciliary muscular mechanisms within the eye.

It is another object of the present invention to provide methods and apparatus that utilize pressure applied by the accommodating muscular action to obtain mechanical deviation of an optical surface of the IOL.

It is a further object of this invention to provide methods and apparatus for applying muscular pressure, through one or more actuators, to obtain a mechanical advantage in altering the optical parameters of one of more surfaces of the IOL.

These and other objects of the present invention are accomplished by providing a lens in which force exerted on a fluid reservoir by the ciliary process is applied to a moveable optical surface through an actuator whose area is the same as or smaller than the area of the optical surface. In this manner, the optical surface is made to move through a deflection that is more pronounced than would be otherwise possible. In addition, the force exerted by the ciliary process upon the outer surface of the IOL may be oriented in a direction optimal for the motion of the optical surface.

In accordance with the principles of the invention, a lens is provided comprising an optic element forming a housing and having an actuator that divides the housing into first and second fluid chambers. The first and second fluid chambers are filled with first and second fluids, respectively, having either the same index of defraction or different indices of refraction. The optical parameters of the lens are altered by varying the amounts of first and second fluids in the first and second chambers. In a first embodiment the actuator comprises a flexible transparent layer operated on directly by movement of fluid from a reservoir; in a second embodiment the actuator comprises one or more extensible cells that act to deflect a flexible transparent layer.

In accordance with another aspect of the invention, a reservoir containing one of the first or second fluids is disposed in a haptic of the IOL, so that forces applied to the haptic by the ciliary process are transmitted via the fluid to deform the flexible layer. In alternative embodiments the reservoirs may be located in a non-optic portion of the lens and actuated by compressive or torsional forces applied by the ciliary muscles through the haptics.

Alternatively, or in addition, fulcrum points may be disposed within the optic element to facilitate deflection of the flexible layer, thereby providing a multiplying effect of the forces applied by the ciliary process.

Methods of using the lens of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to an in-situ accommodating intraocular lens system. In accordance with the principles of the present invention, methods and apparatus are provided wherein a lens has an optic element comprising a substrate and an actuator that divides the interior of the housing into two or more fluid-filled chambers. The fluids filling the chambers may have the same or different indices of refraction. The optical power of the lens is altered by changing the relative amounts of fluids in the chambers, thereby changing the curvature of one of the chambers and the refractive path of light passing through the optic element.

Figure 1:
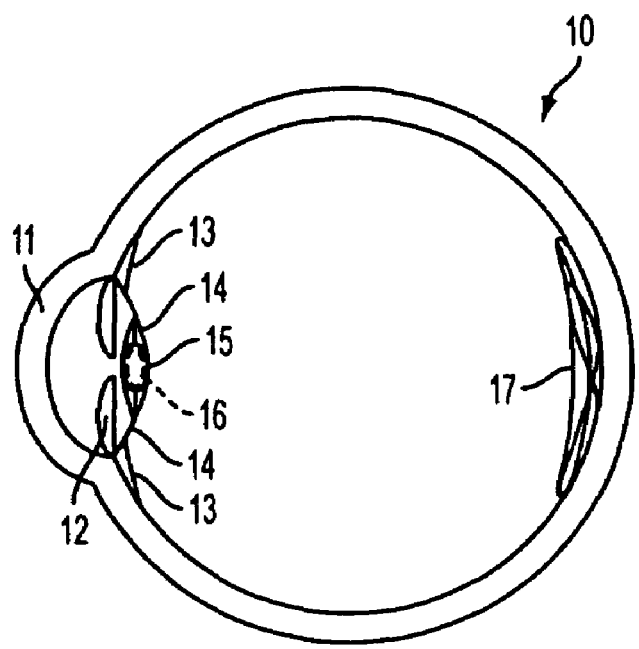
FIG. 1 is a sectional side view of a human eye.

Referring to FIGS. 1 and 2, the structure and operation of a human eye are first described as context for the present invention. Eye 10 includes cornea 11 pupil 12, ciliary muscles 13, ligament fibers 14, capsule 15, lens 16 and retina 17. Natural lens 16 is composed of viscous, gelatinous transparent fibers, arranged in an "onion-like" layered structure, and is disposed in transparent elastic capsule 15. Capsule 15 is joined by ligament fibers 14 around its circumference to ciliary muscles 13, which are in turn attached to the inner surface of eye 10.

Figure 2A:
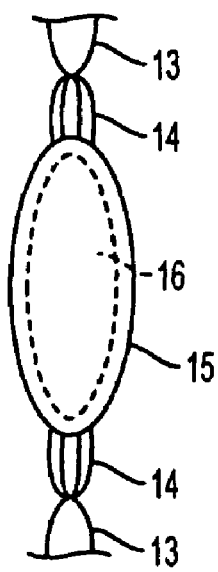
FIGS. 2A and 2B are, respectively, detailed sectional side views of the lens and supporting structures of FIG. 1 illustrating relaxed and contracted states of the ciliary muscles.
Figure 2B:
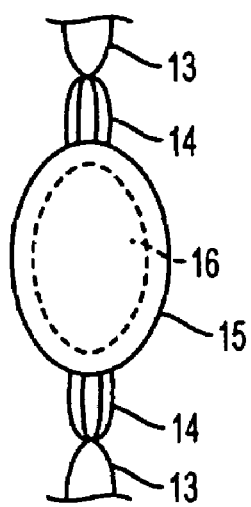

Isolated from the eye, the relaxed capsule and lens takes on a spherical shape. However, as described hereinabove, when suspended within the eye by ligament fibers 14, capsule 15 moves between a moderately convex shape (when the ciliary muscles are relaxed) to a highly convex shape (when the ciliary muscles are contracted). As depicted in FIG. 2A, when ciliary muscles 13 relax, capsule 15 and lens 16 are pulled about the circumference, thereby flattening the lens. As depicted in FIG. 2B, when ciliary muscles 13 contract, capsule 15 and lens 16 relax somewhat, thus allowing the lens and capsule to assume a more spherical shape, and thus increasing the diopter power of the lens.

As discussed hereinabove, accommodating lenses currently nearing commercialization, such as the Crystalens device under development by Eyeonics, Inc., Aliso Viejo, Calif., typically involve converting diametral movements of the ciliary muscle into forward and backward movement of the optic portion of the IOL relative to the retina. This approach is thought to be required because, following extraction of a cataract-effected lens, the capsular bag is very loose, and the ligament fibers that couple the capsule to the ciliary muscles are no longer in tension. Devices such as the Crystalens thus do not employ the natural accommodation mechanisms described above, but instead rely directly on radially inward compressive forces applied by the ciliary muscle to the haptics of the IOL.

In accordance with principles of the present invention, radially compressive forces applied to the haptics of the IOL are employed to provide accommodation by deflecting a flexible transparent layer that separates two fluids preferably having different indices of refraction. This deflection causes a variation in the optical path of light passing through the lens, thus altering its optical parameters.

Figure 3A:
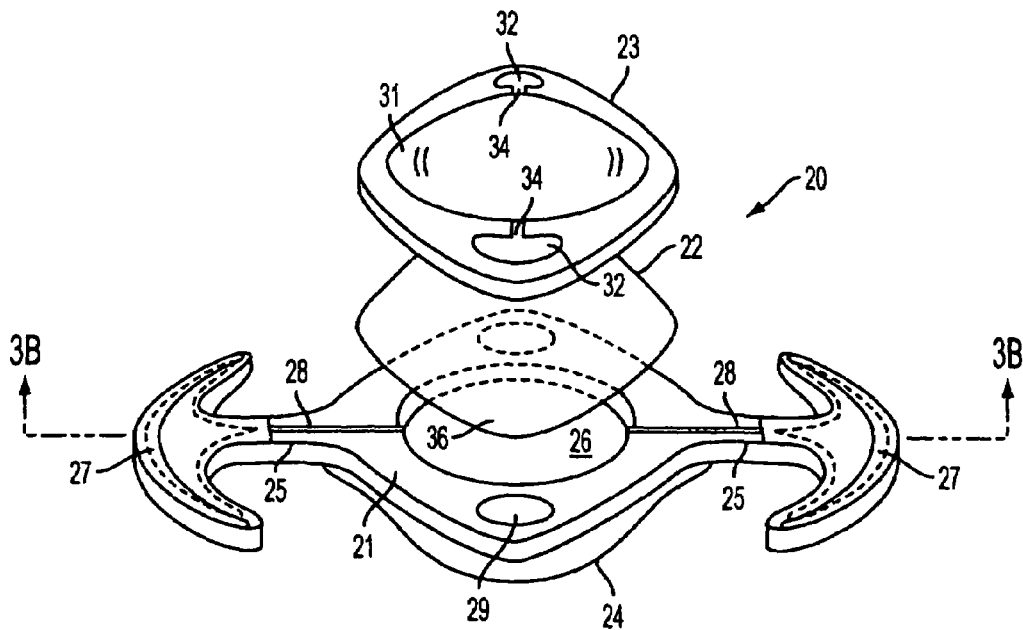
FIGS. 3A and 3B are, respectively, an exploded perspective and side sectional view taken along line 3B-3B of an exemplary embodiment of an accommodating intraocular lens constructed in accordance with the principles of the present invention.
Figure 3B:
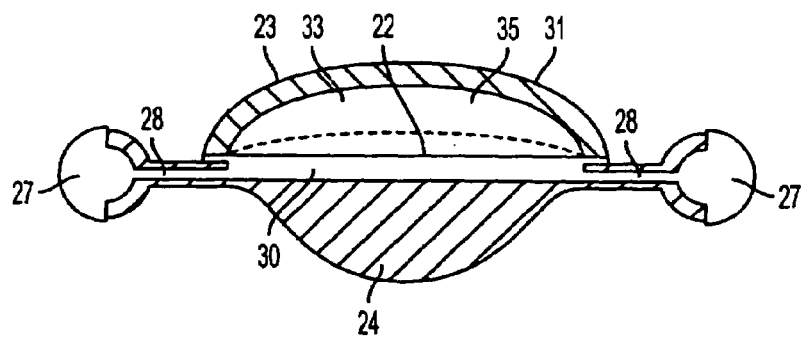

Referring now to FIGS. 3A and 3B, a first illustrative embodiment of an accommodating IOL of the present invention is described. IOL 20 preferably comprises substrate 21, flexible layer 22 and anterior element 23, which may be assembled in a sandwiched configuration, depicted in FIG. 3B.

Substrate 21 preferably comprises a sturdy transparent polymer and includes posterior lens 24, haptics 25, lower chamber 26, reservoirs 27, passageways 28 and relief chambers 29. Lower chamber 26 communicates with reservoirs 27 disposed on the ends of haptics 25 via passageways 28. Lower chamber 26, reservoirs 27 and passageways 28 are filled with transparent fluid 30, such as silicone. The outwardly directed surfaces of haptics 25 preferably comprise a resilient elastic material that permits force applied to those surfaces by the ciliary muscles to cause fluid to move from reservoirs 27 through passageways 28 into lower chamber 26.

Anterior element 23 preferably comprises a rigid transparent material, and includes anterior lens 31, and relief reservoirs 32. The interior surface of anterior element 23 is convex and forms upper chamber 33, which accommodates upward motion of flexible transparent layer 22, as described hereinbelow. Relief reservoirs 32 are disposed in alignment with relief chambers 29 in substrate 21, outside the optical path of anterior lens 31. Upper chamber 33 communicates with relief reservoirs 32 via passageways 34, and is filled with transparent fluid 35, such as silicone. Preferably, transparent fluid 30 in lower chamber 26 has a different index of refraction than transparent fluid 35 in upper chamber 33.

Flexible transparent layer 22 divides upper chamber 33 of anterior element 23 from lower chamber 26 of substrate 21 and acts as an actuator in redistributing the relative volumes of fluid in the upper and lower chambers. Ends 36 of flexible transparent layer also separate relief reservoirs 32 in anterior element 23 from relief chambers 29 in substrate 21. Because relief chambers 29 are empty, they permit excess fluid entering the relief reservoirs 32 to cause the layer to reversibly bulge into the relief chambers when flexible transparent layer is deflected upward.

When assembled as shown in FIG. 3B and implanted into the empty capsule of a cataract patient, compressive forces applied by the ciliary muscles cause fluid 30 to move from reservoirs 27 into lower chamber 26, thereby causing flexible transparent layer 22 to deflect upward, as shown in dotted line. Upward motion of layer 22 causes excess fluid in upper chamber 33 to move through passageways 34 into relief reservoirs. Because relief chambers 29 in substrate 21 are not fluid-filled, they permit layer 22 to bulge downward into the relief chambers.

In accordance with the principles of the present invention, movement of layer 22, and the accompanying displacement of a volume of fluid 35 with a volume of fluid 30 of a different index of fraction, changes the optical parameters of the lens, thereby moving the focus of the lens from near to far or vice-versa. Posterior lens 24 also provides optical power, and also optical index dispersion so as to optimize aberration characteristics, including wave aberration of all order, or chromatic aberration.

When the ciliary muscles relax, layer 22 resiliently contracts to its original position, forcing excess fluid 30 from lower chamber back into reservoirs 27 via passageways. In addition, as the pressure in upper chamber 33 is reduced, fluid 35 passes out of relief reservoirs 32 via passageways 34 and into upper chamber 33, thereby relieving bulging of layer 22 into relief chambers 29.

Figure 4A:
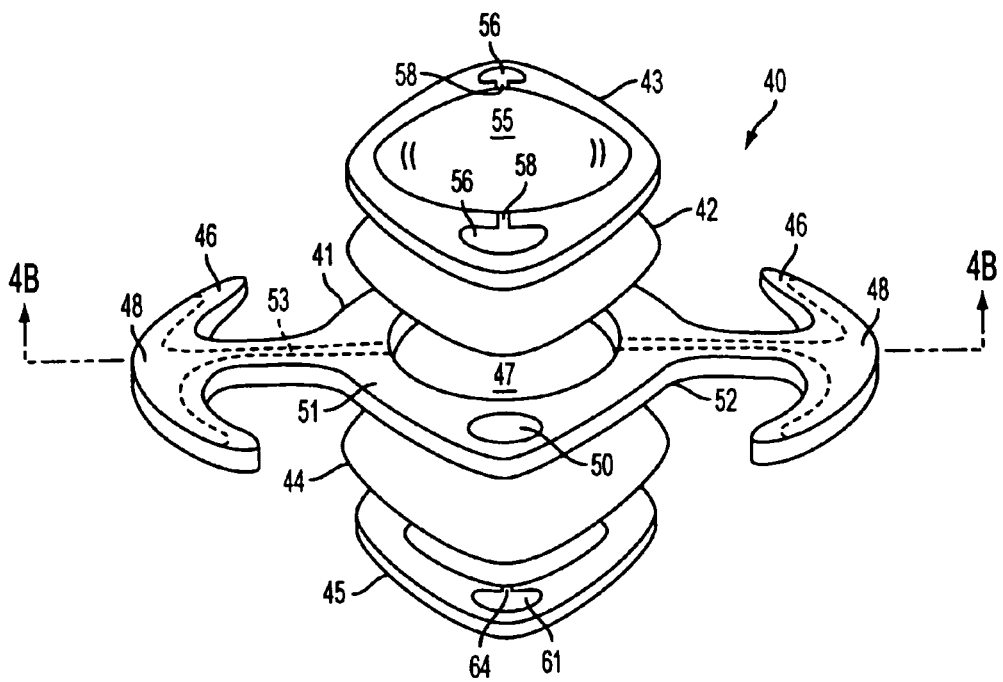
FIGS. 4A and 4B are, respectively, an exploded perspective and side sectional view taken along line 4B-4B of an alternative embodiment of an accommodating intraocular lens of the present invention.
Figure 4B:
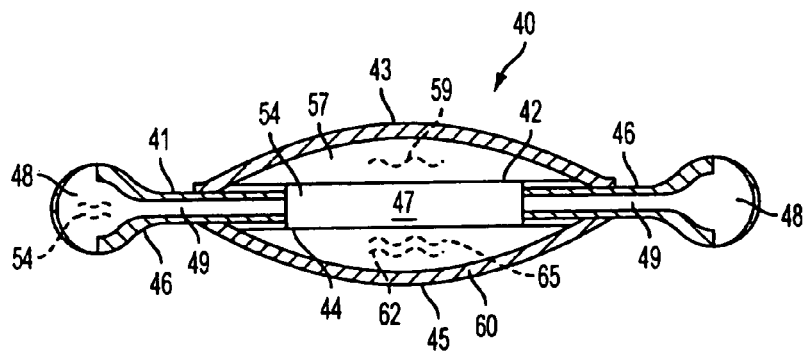

Referring now to FIGS. 4A and 4B, another illustrative embodiment of an accommodating IOL of the present invention constructed in accordance with the principles of the present invention is described. IOL 40 is similar in construction to IOL 20 of FIG. 3, but has two interfaces to alter the power of the lens responsive to fluid movement. More specifically, IOL 40 comprises substrate 41, flexible layer 42, anterior element 43, flexible layer 44 and posterior element 45. All of these components are assembled in a sandwiched configuration, as depicted in FIG. 4B.

Substrate 41 preferably comprises a sturdy transparent polymer and includes haptics 46, central chamber 47, reservoirs 48, passageways 49 and relief chambers 50 formed in each of upper surface 51 and lower surface 52. Central chamber 47 communicates with reservoirs 48 disposed on the ends of haptics 46 via passageways 49. Central chamber 47, reservoirs 48 and passageways 49 are filled with transparent fluid 54, such as silicone. The outwardly directed surfaces of haptics 46 preferably comprise a resilient elastic material that permits force applied to those surfaces by the ciliary muscles to cause fluid to move from reservoirs 48 through passageways 49 into central chamber 47.

Anterior element 43 preferably comprises a rigid transparent material, and includes anterior lens 55, and relief reservoirs 56. The interior surface of anterior element 43 is convex and forms upper chamber 57, which accommodates upward motion of flexible transparent layer 42, as described hereinbelow. Relief reservoirs 56 are disposed in alignment with relief chambers 50 in substrate 41, outside the optical path of anterior lens 43. Upper chamber 57 communicates with relief reservoirs 56 via passageways 58, and is filled with transparent fluid 59, such as silicone. Preferably, transparent fluid 54 in central chamber 47 has a different index of refraction than transparent fluid 59 in upper chamber 57.

Posterior element 45 is similar in construction to anterior element 43, and preferably comprises a rigid transparent material. Posterior element 45 includes posterior lens 60 and relief reservoirs 61. The interior surface of posterior element 45 is convex upward and forms lower chamber 62, which accommodates downward motion of flexible transparent layer 44. Relief reservoirs 61 are disposed in alignment with relief chambers formed in the lower surface of substrate 41, outside the optical path of posterior lens 45. Lower chamber 62 communicates with relief reservoirs 61 via passageways 64, and is filled with transparent fluid 65, which may be the same as fluid 59 in upper chamber 57. Preferably, transparent fluid 54 in central chamber 47 has a different index of refraction than transparent fluid 65 in lower chamber 62.

Flexible transparent layer 42 separates upper chamber 57 of anterior element 43 from central chamber 47 of substrate 41, while flexible transparent layer 44 separates lower chamber 62 from central chamber 47. As described below, layers 42 and 44 act as actuators for altering the relative volumes of fluids in the chambers, and thus the optical power of the lens. The ends of flexible transparent layer 42 separate relief reservoirs 56 in anterior element 43 from relief chambers 50 in the upper surface of substrate 41. Likewise, the ends of flexible transparent layer 44 separate relief reservoirs 61 in posterior element 45 from the relief chambers in the lower surface of substrate 41. Because the relief chambers are empty, they permit excess fluid entering the relief reservoirs 56 and 61 to cause layers 42 and 44 to reversibly bulge into the relief chambers when flexible transparent layers 42 and 44 are deflected outward from central chamber 47.

When assembled as shown in FIG. 4B and implanted into the empty capsule of a cataract patient, compressive forces applied by the ciliary muscles cause fluid 54 to move from reservoirs 48 into central chamber 47, thereby causing flexible transparent layers 42 and 44 to deflect outward. Upward motion of layer 42 and downward motion of layer 44 causes excess fluid in upper and lower chambers 57 and 62 into the respective relief reservoirs 56 and 61. Because the corresponding relief chambers in substrate 41 are not fluid-filled, they permit layers 42 and 44 to bulge into the relief chambers. Movement of layers 42 and 44, and the accompanying displacement of volumes of fluid 59 and 65 with volumes of fluid 54 of a different index of fraction, changes the optical parameters of the lens, thereby moving the focus of the lens from near to far or vice-versa.

When the ciliary muscles relax, each of layers 42 and 44 resiliently contracts to its original position, forcing excess fluid from central chamber 47 back into reservoirs 49. In addition, as pressure in upper and lower chambers 57 and 62 is reduced, fluids 59 and 65 return from relief reservoirs 56 and 61 into the upper and lower chambers, respectively.

Figure 5:
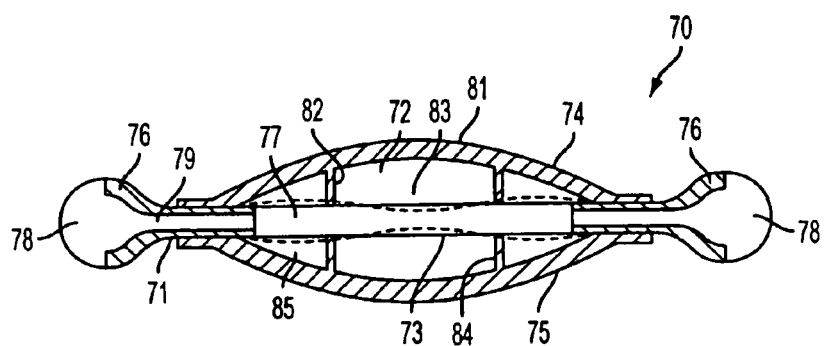
FIG. 5 is a side sectional view of an alternative embodiment of the accommodating IOL similar to that of FIGS. 4A and 4B, depicting the use of an annular fulcrum.

Referring now to FIG. 5, an alternative embodiment of an accommodating IOL of the invention, similar in design to the embodiment of FIG. 4 is described. IOL 70 comprises substrate 71, flexible layers 72 and 73, and anterior and posterior elements 74 and 75, assembled in a sandwiched configuration.

Substrate 71 is similar in construction to substrate 41 of FIG. 4, and comprises haptics 76, central chamber 77, reservoirs 78, passageways 79 and relief chambers formed in each of its upper and lower surfaces, arranged as described for the embodiment of FIG. 4. With this arrangement, force applied to the outer surfaces of haptics 76 by the ciliary muscles cause fluid to move from reservoirs 78 through passageways 79 into central chamber 77.

Anterior element 74 preferably comprises a rigid transparent material, and anterior lens 81, relief reservoirs (arranged as in the embodiment of FIG. 4), and annular fulcrum 82. The interior surface of anterior element 74 is convex and forms fluid-filled upper chamber 83, which accommodates upward motion of flexible layer 72, as described hereinbelow. Relief reservoirs are disposed in alignment with relief chambers in substrate 71, outside the optical path of anterior lens 74, and act to relieve excess pressure in the upper chamber when flexible layer 72 deflects upward. As described for the embodiment of FIG. 4, upper chamber 83 contains a fluid having a different index of refraction than the fluid in central chamber 77. Posterior element 75 is similar in construction to anterior element 74, and preferably also includes annular fulcrum 84 disposed in fluid-filled lower chamber 85.

Flexible transparent layer 72 separates upper chamber 83 of anterior element 74 from central chamber 77 of substrate 41, while flexible transparent layer 73 separates lower chamber 85 from central chamber 77. Layers 72 and 73 preferably comprise a resilient flexible material that flexes against annular fulcrums 82 and 84 when fluid is moved into central chamber 77 by forces applied to reservoirs 78.

In the embodiment of FIG. 5, annular fulcrum 82 illustratively comprises an annular ring extending inward from the interior surface of anterior element 74 to contact flexible layer 72, and may include apertures to permit transparent fluid contained in upper chamber 83 to move freely within the chamber. Annular fulcrum 84 disposed in lower chamber 85 comprises a corresponding structure that contacts flexible layer 73. Fulcrums 82 and 84 fix the surfaces of layers 72 and 73 to optimize the efficiency and effectiveness of changing the optical power of layers 72 and 73 using the available flow of fluid.

As will be appreciated, the mechanical advantage obtained by fulcrums 82 and 84, and the degree of deflection imposed upon layers 72 and 73 is dependent upon the distance of the fulcrum contact point from the optical axis of the lens. In addition, while illustratively described as annular rings, fulcrums 82 and 84 may comprise other suitable shapes, such as discrete pegs or cones.

Operation of the embodiment of FIG. 5 is similar to that of the embodiment of FIG. 4, except that fulcrums 82 and 84 control deflection of layers 72 and 73. When implanted into the empty capsule of a cataract patient, compressive forces applied by the ciliary muscles cause fluid to move from reservoirs 78 into central chamber 77, thereby causing layers 72 and 73 to deflect outward.

Because outward motion of layers 72 and 73 is fixed by the points of contact with fulcrums 82 and 84, layers 72 and 73 may assume different deflection patterns (illustrated in dotted line in FIG. 5) than for the unconstrained layers in the embodiment of FIG. 4. Deflection of layers 72 and 73, and the accompanying displacement of volumes of fluid in upper and lower chambers 83 and 85 with corresponding volumes of fluid of a different index of fraction in central chamber 77, changes the optical parameters of the lens, thereby moving the focus of the lens from near to far or vice-versa.

When the ciliary muscles relax, each of layers 72 and 73 returns to its original position, thereby forcing excess fluid from central chamber 77 back into reservoirs 78. In addition, as pressure in upper and lower chambers 83 and 85 is reduced, fluid returns from the relief reservoirs into the upper and lower chambers respectively, as described for the lens of FIG. 4.

Figure 6A:
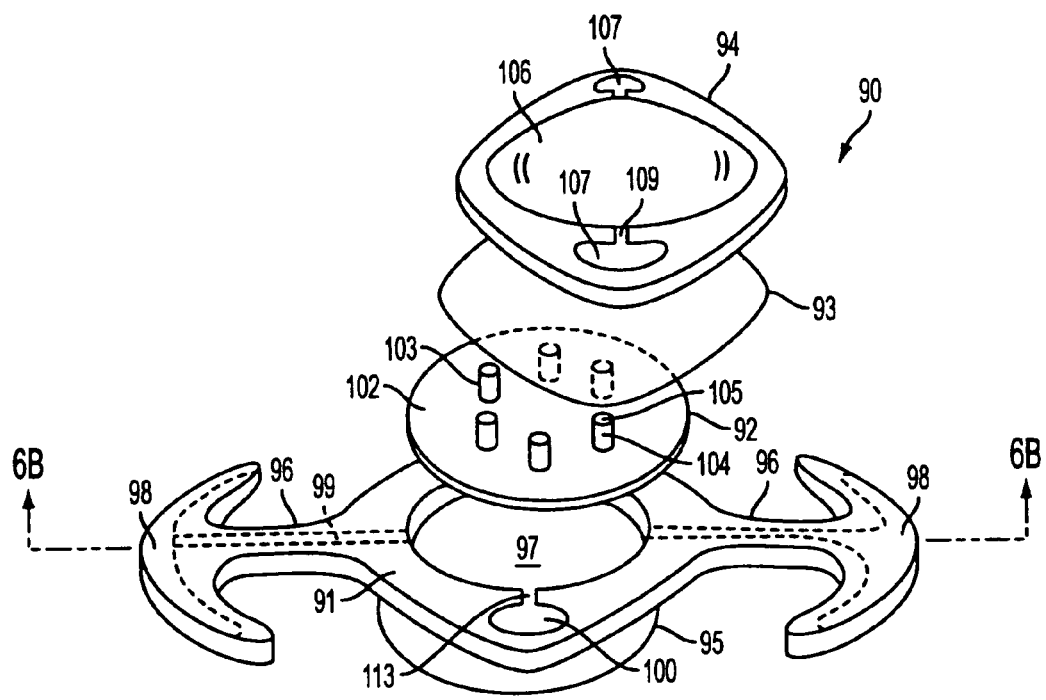
FIGS. 6A and 6B are, respectively, an exploded perspective and side sectional view taken along line 6B-6B of another alternative embodiment of an accommodating intraocular lens of the present invention.
Figure 6B:
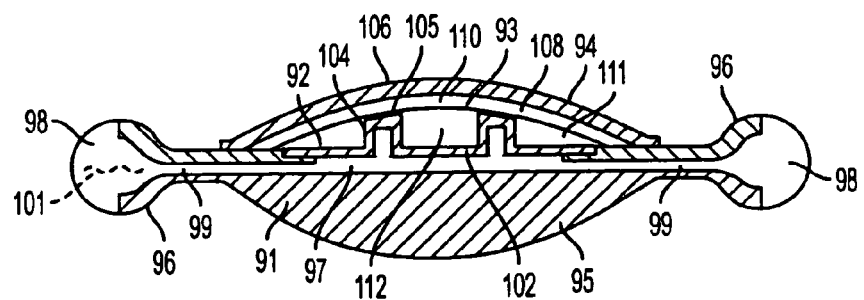

Referring now to FIGS. 6A and 6B, another alternative embodiment of an accommodating IOL of the present invention is described, in which a flexible layer is deflected using extensible cells that have a smaller area than the layer itself. IOL 90 comprises substrate 91, actuator element 92, flexible layer 93 and anterior element 94, which may be assembled in a sandwiched configuration, FIG. 6B.

Substrate 91 preferably comprises a sturdy transparent polymer and includes posterior lens 95, haptics 96, lower chamber 97, reservoirs 98, passageways 99 and lower relief reservoirs 100. Lower chamber 97 communicates with reservoirs 98 disposed on the ends of haptics 96 via passageways 99. Lower chamber 97, reservoirs 98, passageways 99 and lower relief reservoirs 100 are filled with transparent fluid 101. The outwardly directed surfaces of haptics 96 comprise a resilient elastic material that permits force applied to those surfaces by the ciliary muscles to cause fluid to move from reservoirs 98 through passageways 99 into lower chamber 99.

Actuator element 92 comprises disk-shaped member 102 having a plurality of cells 103 extending upwardly from its upper surface. Each cell 103 illustratively comprises an annular sidewall 104 and top 105. The relative thickness of member 102 and sidewalls 104 and tops 105 are selected so that when pressurized fluid is introduced into lower chamber 97, tops 105 of cells 103 extend axially upward. Illustratively, cells 103 are arranged in a ring at a predetermined radius from the optical axis of lens 90, although more or fewer cells 103 may be employed, and then location selected to enhance deflection of layer 93, as described hereinbelow.

Anterior element 94 preferably comprises a rigid transparent material, and includes anterior lens 106, and upper relief reservoirs 107. The interior surface of anterior element 94 is convex and forms upper chamber 108, which accommodates upward motion of flexible layer 93, as described hereinbelow. Upper relief reservoirs 107 are disposed in alignment with lower relief chambers 100 in substrate 91, outside the optical path of anterior lens 94. Upper chamber 108 communicates with upper relief reservoirs 107 via passageways 109, and is filled with transparent fluid 110.

Flexible layer 93 is affixed around its circumference to substrate 91 and is disposed in contact with tops 105 of cells 103. Transparent fluid 111 is contained within space 112 between the upper surface of actuator element 92 and lower surface of layer 93. Lower relief reservoirs 100 communicate with space 112 via passageways 113 disposed in substrate 91. A portion of layer 93 divides upper relief reservoirs 107 from lower relief reservoirs 100, for purposes to be described hereinafter. Fluid 111 disposed in space 112 preferably has the same index of refraction as fluid 101 in lower chamber 97, and a different index of refraction than fluid 110 contained in upper chamber 108.

When assembled as shown in FIG. 6B and implanted into the empty capsule of a cataract patient, compressive forces applied by the ciliary muscles cause fluid 101 to move from reservoirs 98 into lower chamber 97, thereby causing tops 105 of cells 103 to extend axially upward. Upward movement of tops 105 of cells 103 in turn causes layer 93 to deflect upward and displace fluid 110 in upper chamber 108. Fluid displaced from upper chamber 108 flows into upper relief reservoirs 107 via passageways 109.

Simultaneously, because lower relief reservoirs 100 communicate with space 112, fluid 111 is drawn from lower relief reservoirs as layer 93 is deflected upward by cells 103. Consequently, the portions of layer 93 that divide upper relief reservoirs 107 from lower relief reservoirs 100 serve as diaphragms that permit fluid to be simultaneously displaced into one reservoir and withdrawn from the other. This enables fluids 110 and 111 to pass freely in and out of the optical space in order to balance relative volumes of fluid, the total volume of fluids 110 and 111 remaining constant.

In accordance with the principles of the present invention, movement of layer 93, and the accompanying displacement of volumes of fluid 110 in upper chamber 108 with a corresponding volume of fluid 111 of a different index of fraction in space 112, changes the optical parameters of the lens, thereby moving the focus of the lens from near to far or vice-versa. Posterior lens 95, which in this case comprises a solid material, also provides additional optical power. Posterior lens 95 also may provide optical index dispersion so as to optimize aberration characteristics, including wave aberration of all order, or chromatic aberration.

When the ciliary muscles relax, tops 105 of cells 103 contract, and layer 93 resiliently contracts to its original position. This in turn forces excess fluid 111 in space 112 back into lower relief reservoirs 100. In addition, as the pressure in upper chamber 108 is reduced, fluid 110 is drawn out of upper relief reservoirs 107 and into upper chamber 108.

In the embodiment of FIG. 6, fluid 101 is forced into cell 103 by ciliary forces acting on the surface of reservoir 98, so that the actuator works in a direction parallel to the optical axis of the lens. As will be appreciated, actuator element 92 must be index matched to fluid 101, which moves with cells 103, as well as fluid 111 that surrounds cells 103 in space 112. Also in the embodiment of FIG. 6, posterior lens 95 is formed from the same material as substrate 91. Alternatively, posterior lens 95 may comprise a different material than substrate 91, having a shape and optical parameters chosen to optimize the optical performance of the lens system.

In accordance with another aspect of the present invention, cells 103 of the embodiment of FIG. 6 act not only to deflect layer 93, but also serve as fulcrum contact points, in a manner analogous to the annular fulcrum 82 of the embodiment of FIG. 5.

Figure 7A:
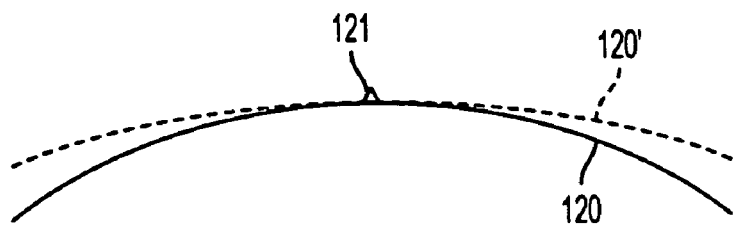
FIGS. 7A-7C are schematic views of illustrating the use of fulcrum points to facilitate deflection of an optical surface in accordance with the principles of the present invention.
Figure 7B:
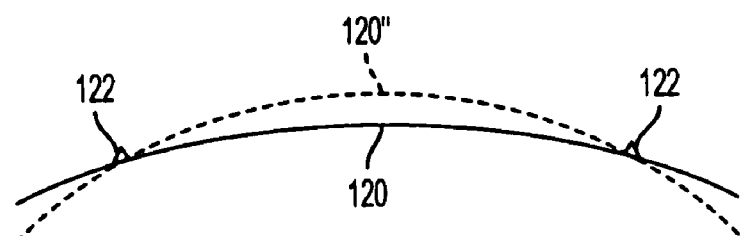
Figure 7C:
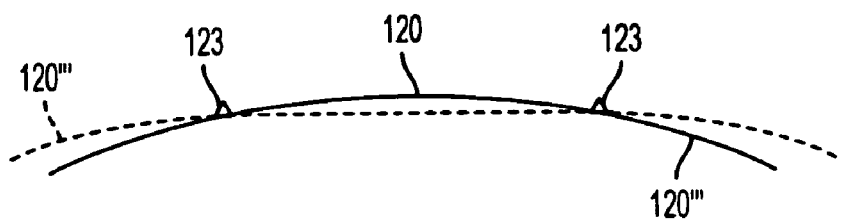

Referring now to FIGS. 7A-7C, the effect of location of the fulcrum, whether a solid point of contact (as in FIG. 5) or point of contact of a cell (as in FIG. 6) is further described. Generally, fixation within the optical zone of surface 120 (corresponding to the layer or flexible layers of the various embodiments described hereinabove), may be accomplished in several fashions depending on the effect and efficiency required of the fluid forces provided by the fluid being moved into the chamber or cell by the forces acting on the reservoirs in the IOL haptics.

If it is desired that surface 120 assume a flatter configuration 120' that provides less optical focusing power (shown in dotted line in FIG. 7A), then fixation at fulcrum point 121 would be desired. If, on the other hand, it is desired that surface 120 provide more power when the ciliary muscles contract (corresponding to highly convex configuration 120", shown in dotted line in FIG. 7B), then fixation at fulcrum points 122 would be desirable.

As a further alternative, to obtain most efficient use of fluid power, e.g., to obtain maximal change in optical power for a given movement of surface 120 (corresponding to surface configuration 120'" in FIG. 7C), some fixation at some intermediate fulcrum point 123 may be desired. Fulcrum point 123 also may be selected so as to minimize the change in the volumes of the total fluid within the optical zone, thereby obviating the need for relief reservoirs to absorb excess fluid volumes. In this latter case, deflection of the flexible layer causes sufficient redistribution of the fluids within the first and second chambers to alter the power of the lens.

It additionally should be understood that by selecting the indices of refraction of the solid and liquid materials used in the lens of the present invention, it may be possible for a positive surface (i.e., convex surface) to act as a negative lens, and vice-versa.

The dynamic response of the eye is relatively fast, but is not beyond the ability of fluids to move in the dimensions of interests, on the order of 5 mm or less. It may, however, be required that the fluid motion be managed in some manner so as to avoid fatiguing the ciliary muscles.

Figure 8:
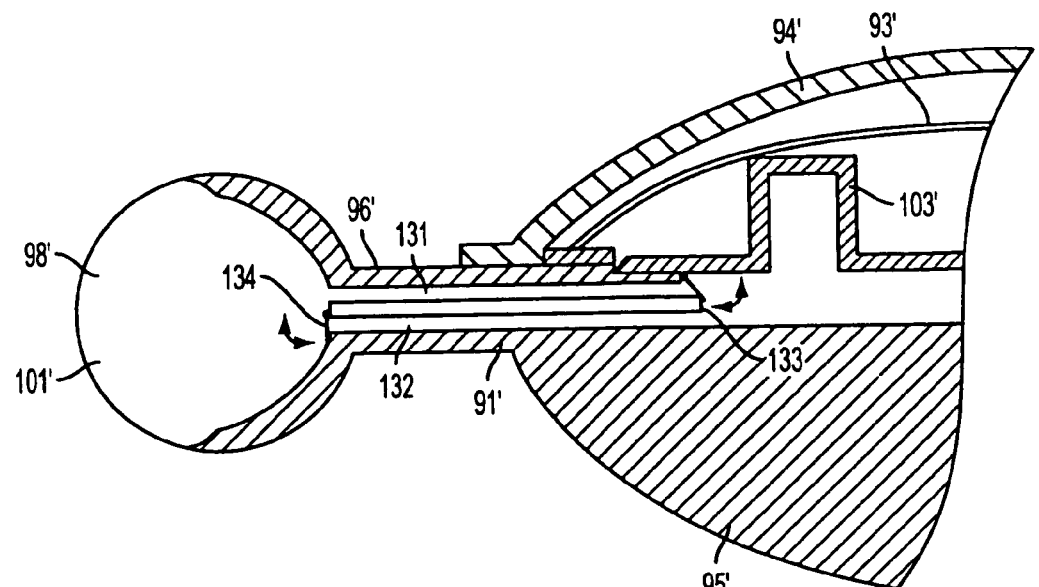
FIG. 8 is a side-sectional view of another illustrative embodiment in which inflow and outflow pathways connect the optic element to a fluid reservoir.

Referring now to FIG. 8, an exemplary arrangement is described for controlling fluid flows into and out of a cell, such as cell 103 of the embodiment of FIG. 6. IOL 130 is constructed similarly to IOL 90 of FIG. 6, and is designated with like-primed numbers. IOL 130 differs, however, in that instead of having single passageway 99 connecting reservoir 98 to lower chamber 97, as in FIG. 6, separate inflow channel 131 and outflow channel 132 are provided, each controlled by a one-way valve, such as flap valves 133 and 134. In addition, inflow channel 131 may have a smaller or larger cross-sectional area than outflow channel 132. Alternatively, inflow and outflow channels 131 and 132 may have the same flow area, but with more or fewer inflow channels than outflow channels.

Figure 9A:
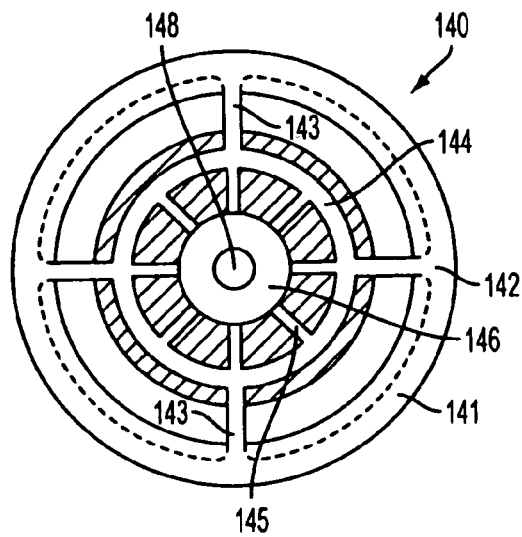
FIGS. 9A and 9B are, respectively, a plan view, partly in section, and a side-sectional view of another embodiment of the lens of the present invention in which the reservoir is designed to equalize forces applied by the ciliary muscles.
Figure 9B:
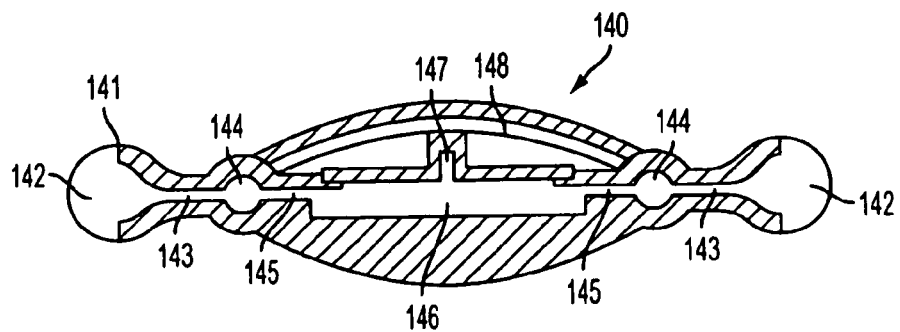

With respect to FIGS. 9A and 9B, a further alternative embodiment of the lens of the present invention is described. Whereas the previously described lens embodiments illustratively employ two haptics, each with its own reservoir, IOL 140 comprises single haptic 141 that surrounds the optic element. Haptic 141 contains reservoir 142 that is coupled by channels 143 to manifold 144. Manifold 144 serves to equalize pressures applied to the haptic by the ciliary muscles, and equalize the resulting fluid flows through passageways 145 to chamber 146 and thus cell 147. Cell 147 in turn controls deflection of layer 148, as in the above-described embodiment of FIG. 6. As described for the preceding embodiments, all surfaces and fluids are appropriately index matched.

Figure 10A:
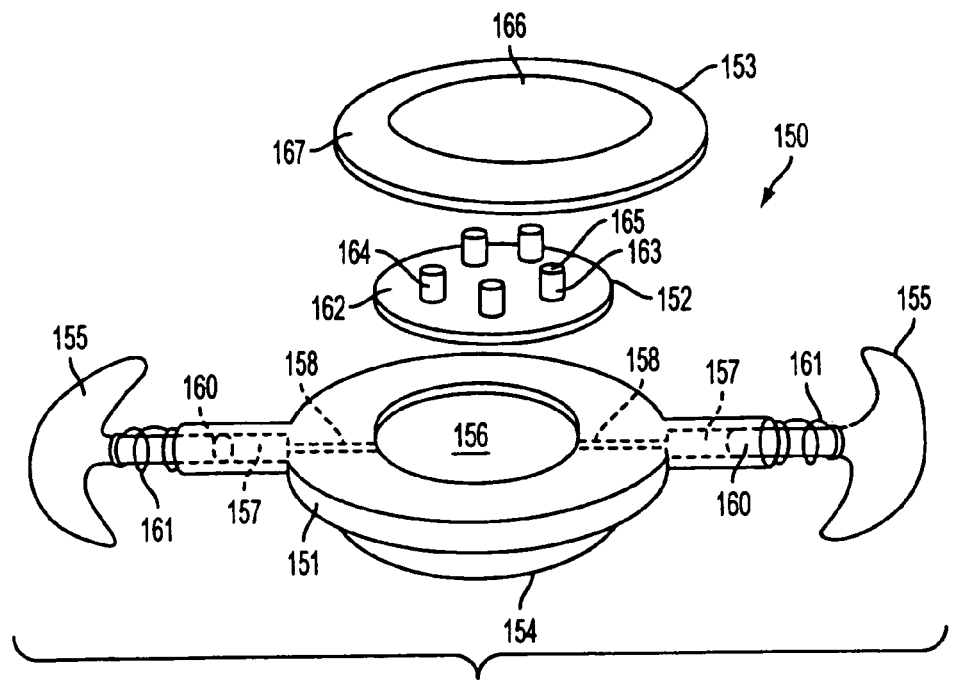
FIGS. 10A and 10B are, respectively, an exploded perspective view and a side-sectional view of another alternative embodiment of the lens of the present invention.
Figure 10B:
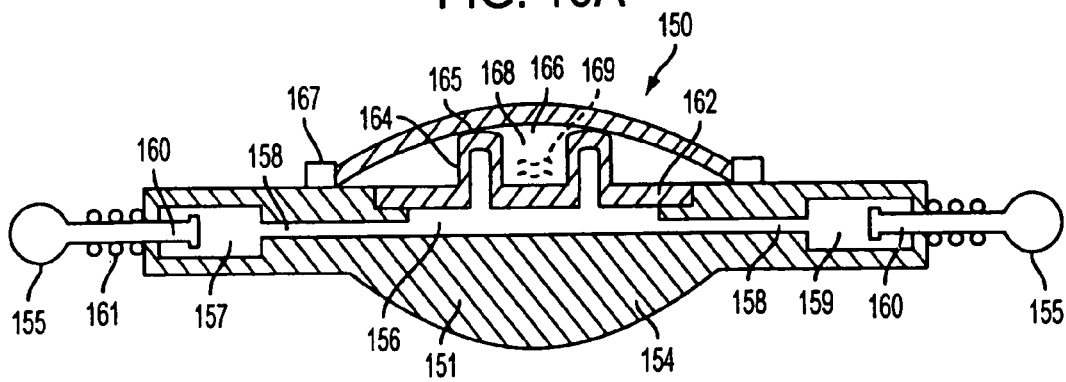

Referring now to FIGS. 10A and 10B, a further alternative embodiment of an accommodating lens constructed in accordance with the principles of the present invention is described. IOL 150 comprises substrate 151, actuator element 152 and anterior element 153, which may be assembled in a sandwiched configuration, FIG. 10B.

Substrate 151 preferably comprises a sturdy transparent polymer and includes posterior lens 154, haptics 155, lower chamber 156, reservoirs 157 and passageways 158. Lower chamber 156 communicates with reservoirs 157 via passageways 158, and lower chamber 156, reservoirs 157 and passageways 158 are filled with transparent fluid 159. Haptics 155 have ends 160 that are slidably disposed in reservoirs 157 and serve as plungers that permit compressive force applied to the haptics by the ciliary muscles to cause fluid to move from reservoirs 157 through passageways 156 and into lower chamber 156. Haptics 155 may include coil springs 161 or other suitable means to bias the haptics to an extended position that maintains engagement of the outer surfaces of the haptics with the capsule and/or ciliary muscles.

Actuator element 152 comprises disk-shaped member 162 having a plurality of cells 163 extending upwardly from its upper surface. Each cell 163 illustratively comprises annular sidewall 164 and top 165. The relative thickness of member 162 and sidewalls 164 and tops 165 are selected so that tops 165 are relatively more flexible than the other portions of actuator element 152. Accordingly, when pressurized fluid is introduced into lower chamber 156, tops 165 of cells 163 extend axially upward. Illustratively, cells 163 are arranged in a ring at a predetermined radius from the optical axis of lens 150, although more or fewer cells 163 may be employed, and their location selected to enhance deflection of the flexible layer of anterior element 153, as described hereinbelow.

Anterior element 153 comprises flexible transparent layer 166 that forms the anterior lens of IOL 150, and support ring 167. Flexible transparent layer 166 assumes a convex shape when it contacts tops 165 of cells 163, and forms upper chamber 168. Because flexible transparent layer 166 can move outward when deflected by cells 163, relief reservoirs as in the embodiment of FIG. 6, may be omitted. Upper chamber 168 is filled with transparent fluid 169 having an index of refraction the same as fluid 159 disposed in lower chamber 156 and the interior of cells 163, and preferably the same index of refraction as the material of transparent layer 166. Layer 166 may have a cross-sectional thickness profile, or stiffness profile, that provides for optimal deformation when forces from cells 163 are applied, so that good optical performance may be obtained throughout the deflection range.

When assembled as shown in FIG. 10B and implanted into the empty capsule of a cataract patient, compressive forces applied by the ciliary muscles cause fluid 159 to move from reservoirs 157 into lower chamber 156, thereby causing tops 165 of cells 163 to extend axially upward. Upward movement of tops 165 of cells 163 in turn causes flexible layer 166 of the anterior element to deflect upward and redistribute fluid 169 contained in upper chamber 168.

In accordance with the principles of the present invention, movement of flexible layer 166, and the accompanying redistribution of fluid 169 in upper chamber 168, with a corresponding increase in the volume of fluid 159 in cells 163, changes the optical parameters of the lens, thereby moving the focus of the lens from near to far or vice-versa. Posterior lens 154, which in this case comprises a solid material, also provides additional optical power, and also may provide optical index dispersion so as to optimize aberration characteristics.

When the ciliary muscles relax, coil springs 161 drive haptics 155 radially outward, thereby drawing fluid from within cells 163 into reservoirs 157. This in turn permits tops 165 of cells 163 to contract, and flexible layer 166 resiliently contracts to its original position. As for the previous embodiments, fluid is forced into the cells by ciliary forces acting on the reservoirs through the haptics, so that the actuator works in a direction parallel to the optical axis of the lens. In addition, cells 163 of the embodiment of FIG. 10 act not only to deflect flexible layer 166, but also serve as fulcrum contact points.

Figure 11:
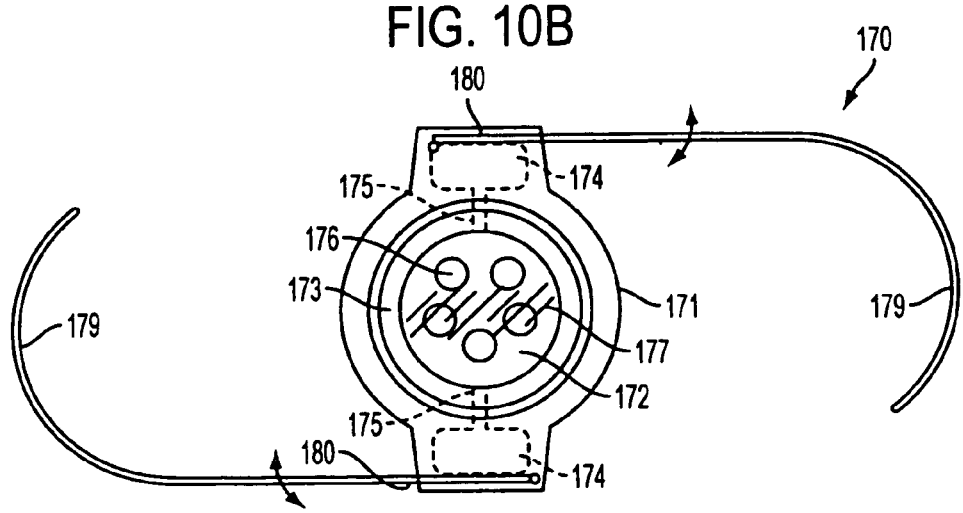
FIG. 11 is a plan view of an alternative haptic arrangement for a lens of type shown in FIG. 10.

Referring to FIG. 11, another alternative embodiment of the accommodating IOL of the present invention is described. IOL 170 is similar in construction to IOL 150 of FIG. 10, and includes substrate 171, actuator element 172 and anterior element 173. Substrate 171 includes reservoirs 174 that are coupled to lower chamber (disposed beneath actuator element 172) via passageways 175. The lower chamber is fluidly coupled to the interior of cells 176 as described above with respect to FIG. 10B. Anterior element 173 includes flexible transparent layer 177 disposed in contact with the tops of cells 176, and is coupled to substrate 171 via support ring 178.

Haptics 179 are affixed to substrate 171 so that lever portions 180 of the haptics contact flexible walls of reservoirs 174. Haptics 179 are configured to engage the capsule, so that contraction of the ciliary muscles applies a torsional force on lever portions of the haptics. This force manifests as a compression of reservoirs 174, which in turn causes fluid to move from reservoirs 174 through the lower chamber and into the interiors of cells 176. The tops of cells 176 then extend upwardly, causing flexible transparent layer 177 to deflect. As described for the preceding embodiment of FIG. 10, deflection of layer 177 permits redistribution of fluid within the lens, thus altering the optical power of the lens. When the ciliary muscles relax, lever portions 180 reduce the force applied to reservoirs 174, and the lens returns to its unstressed condition.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of adjusting the power of an intraocular lens to provide accommodation, the method comprising:
   providing a lens comprising a posterior surface, an anterior surface, an actuator disposed within the lens and within the optical path of the lens that separates first and second chambers disposed along the optical path of the lens, a first volume of a first fluid having a first index of refraction contained within the first chamber, and a second volume of a second fluid having a second index of refraction contained within the second chamber; and
   actuating the actuator to change the curvature of the anterior surface and alter the first volume relative to the second volume responsive to a contraction of a ciliary muscle, thereby changing an optical parameter of the lens.

2. The method of claim 1, further comprising providing a reservoir coupled to the first chamber, wherein actuating the actuator comprises moving an amount of the first fluid from the reservoir to the first chamber.

3. The method of claim 2, wherein the lens further comprises a haptic configured to transmit force from the ciliary muscle to the reservoir, and wherein moving an amount of the first fluid from the reservoir to the first chamber comprises applying a compressive force to the haptic.

4. The method of claim 3, wherein providing the reservoir comprises providing the reservoir disposed in the haptic.

5. A method of adjusting the power of an intraocular lens to provide accommodation, the method comprising:
   providing a lens having a housing, an actuator disposed within the housing to separate the housing into first and second chambers disposed along the optical path of the lens, a first volume of a first fluid having a first index of refraction contained within the first chamber, and a second volume of a second fluid having a second index of refraction contained within the second chamber; and
   actuating the actuator to alter the first volume relative to the second volume responsive to a contraction of a ciliary muscle, thereby changing an optical parameter of the lens,
   wherein the actuator comprises one or more extensible cells disposed in direct contact with a flexible transparent layer, and wherein actuating the actuator comprises actuating the one or more cells to deflect the flexible transparent layer.

6. The method of claim 5, wherein the flexible transparent layer comprises an anterior surface of the housing having a curvature, wherein the first index of refraction is substantially similar to the second index of refraction, and wherein actuating the actuator comprises actuating the one or more cells to deflect the flexible transparent layer to alter the curvature of the anterior surface of the housing.

7. The method of claim 6, wherein the actuator is provided with a third index of refraction, the third index of refraction being substantially equal to the first and second indices of refraction.

8. The method of claim 5, wherein the lens further comprises a reservoir coupled to the one or more extensible cells, and wherein actuating the one or more extensible cells comprises moving an amount of a third fluid from the reservoir to an interior or the one or more extensible cells.

9. The method of claim 5, wherein actuating the one or more extensible cells causes the flexible layer to deflect with the one or more extensible cells acting as a fulcrum.

10. A method of providing accommodation to adjust the power of an intraocular lens, the method comprising:
    providing a lens comprising an outermost anterior surface, a posterior surface, and an actuator disposed within the lens that separates a first chamber and a second chamber, a first volume of a first fluid having a first index of refraction contained within the first chamber, and a second volume of a second fluid having a second index of refraction contained within the second chamber; and
    actuating the actuator in response to ciliary muscle movement to change the curvature of the outermost anterior surface, thereby changing an optical parameter of the lens.

11. The method of claim 10 wherein the actuator separates a first chamber and a second chamber along the optical path of the lens.

12. The method of claim 10 wherein the first and second chambers are non-communicating.

13. The method of claim 10 wherein actuating the actuator comprises axially deflecting the actuator to change the curvature of the outermost anterior surface.

14. The method of claim 10 wherein the actuator is coupled to the outermost anterior surface.

15. The method of claim 10 wherein the first index of refraction and the second index of refraction are substantially equal.

16. The method claim 10 wherein actuating the actuator comprises altering the first volume relative to the second volume.

17. A method of providing accommodative power change in an intraocular lens, the method comprising:
    providing a lens body comprising a first chamber containing a first fluid and a second chamber containing a second fluid disposed along the optical path of the lens, and an actuator element separating the first and second chambers;
    actuating the actuator element in response to ciliary muscle movement to change the curvature of a flexible layer of the lens body to thereby provide accommodative power change, wherein actuating the actuator element comprises moving a portion of the actuator element, wherein said moving portion is in direct contact with a portion of the flexible layer, to thereby deflect the flexible layer.

18. The method of claim 17 wherein moving a portion of the actuator element comprises axially deflecting the actuator element, and wherein deflecting the flexible layer comprises axially deflecting the flexible layer.

19. The method of claim 17 wherein the flexible layer comprises an anterior surface, and actuating the actuator element deflects the anterior surface.

20. The method of claim 17 wherein actuating the actuator element in response to ciliary muscle movement comprises adjusting the volume of the first fluid relative to the volume of the second fluid.

* * * * *